United States Patent [19]

Sestanj

[11] 4,254,108

[45] Mar. 3, 1981

[54] THIOXO-1H-BENZ[de]ISOQUINOLINE-2(3H)-ACETIC ACID DERIVATIVES AND ANTIDIABETIC USE THEREOF

[75] Inventor: Kazimir Sestanj, St. Laurent, Canada

[73] Assignee: Ayerst, McKenna & Harrison Inc., Montreal, Canada

[21] Appl. No.: 92,397

[22] Filed: Nov. 8, 1979

[51] Int. Cl.$^3$ .................. C07D 221/14; A69K 31/47; A61K 37/26

[52] U.S. Cl. .................................. 424/178; 424/258; 546/98

[58] Field of Search .................. 546/98; 424/258, 178

[56] References Cited

U.S. PATENT DOCUMENTS

| | | | |
|---|---|---|---|
| 3,821,383 | 6/1974 | Sestanj et al. | 424/258 |
| 4,118,495 | 10/1978 | Lippman | 424/258 |

OTHER PUBLICATIONS

Dvovnik et al., Science, 182, 1146 (1973).
Grayshan et al., J. Het. Chem., 11, 33 (1974).
Shirosaki et al., Chem. Abs., 86, 89467d (1976).
Cremyln, J. Chem. Soc., 1961, 5055.

Primary Examiner—Mark L. Berch
Attorney, Agent, or Firm—Arthur E. Wilfond

[57] ABSTRACT

Herein disclosed are 1H-benz[de]isoquinoline-2(3H)-acetic acid derivatives. The derivatives are characterized by being derived from 1,3-dioxo-1H-benz[de]-isoquinoline-2H-acetic acid by replacing one of the oxygen atoms with sulfur and by optional substitution at position 6 with a phenylthio group. The derivatives inhibit lens aldose reductase in a diabetic subject.

8 Claims, No Drawings

THIOXO-1H-BENZ[de]ISOQUINOLINE-2(3H)-ACETIC ACID DERIVATIVES AND ANTIDIABETIC USE THEREOF

RELATED APPLICATIONS

1-Oxo-3-thioxo-1H-benz[de]isoquinoline-2(3H)-acetic acid, a compound of this invention, is disclosed as the active agent for methods of treatment in W. Lippmann, U.S. patent application Ser. No. 92,605, now abandoned, filed Nov. 8, 1979 and in W. Lippmann and K. Sestanj, U.S. patent application Ser. No. 92,398, now abandoned, filed Nov. 8, 1979 both filed on the same day as this application.

Another related application is K. Sestanj, U.S. patent application Ser. No. 92,004, filed on the same day as this application.

BACKGROUND OF THE INVENTION

This invention relates to thioxo-1H-benz[de]isoquinoline-2(3H)-acetic acid derivatives, therapeutically acceptable salts thereof, a process for their preparation and to pharmaceutical compositions thereof. The derivatives have pharmacologic properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy and cataracts. These complications have been linked to the undesirable accumulation of sorbitol in diabetic tissue, which is turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182, 1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. This compound also stimulates insulin release while inhibiting glucagon secretion, see W. Lippmann, U.S. Pat. No. 4,118,495, Oct. 3, 1978. Accordingly, this compound represents an important adjunct to the treatment of diabetes mellitus. U.S. Pat. No. 3,821,383 also discloses the 5-nitro, 5-amino and 6-bromo derivatives of 1,3-dioxo-1H-benz[de]isoquinoline-2(3H)-acetic acid.

The present Application discloses a new group of sulfur substituted 1H-benz[de]isoquinoline compounds. The new compounds are more effective than 1,3-dioxo-1H-benz[de]isoquinoline-2(3H)-acetic acid and the related derivatives, disclosed in U.S. Pat. No. 3,821,383, in inhibiting aldose reductase and in stimulating insulin release while inhibiting glucagon. Furthermore, the new compounds are longer acting. Sulfur substituted 1H-benz[de]isoquinolines have been described by P. H. Grayshan et al., J. Heterocycl. Chem., 11, 33 (1974) and by T. Shirosaki, see Chem. Abstr., 86, 89467d (1977) for Japanese Patent Kokai No. 76/109,020, Sept. 27, 1976; however these prior art compounds are distinguished from compounds of the present Application by having sulfur in different oxidation states or by having completely different substituents. Furthermore, a common feature of the compounds of this invention, not shared by prior art compounds, is that they are thioxo-1H-benz[de]isoquinoline derivatives. These thioxo-1H-benz[d]isoquinoline derivatives are prepared by a process whereby an intermediate 1,3-dioxo-1H-benz[de]isoquinoline derivative is reacted with phosphorus pentasulfide. A prior art search indicates that the latter derivatives never have been subjected to phosphorus pentasulfide, although several years ago, R. J. W. Cremlyn, J. Chem. Soc., 5055 (1961) prepared a series of thiophthalimides by reacting corresponding phthalimides with phosphorus pentasulfide.

SUMMARY OF THE INVENTION

The compounds of this invention are represented by formula I

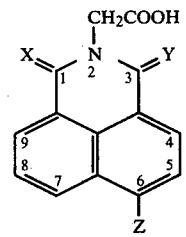

in which X and Y are independently O or S, with the proviso both are not O or S, and Z is H or thiophenyl, or a therapeutically acceptable salt thereof with an organic or inorganic base.

The compounds of formula I are prepared by a process described hereinafter.

A method is provided for preventing or relieving diabetes mellitus associated complications in a diabetic mammal by administering to said mammal an alleviating or prophylactic amount of the compound of formula I or a therapeutically acceptable salt thereof.

The compound of formula I, or a therapeutically acceptable salt thereof with organic or inorganic base, when admixed with a pharmaceutically acceptable carrier, forms a pharmaceutical composition which can be used according to the preceding methods.

DETAILED DESCRIPTION OF THE INVENTION

The "lower alkyl" as used herein means straight chain alkyl radicals containing from one to four carbon atoms and branched chain alkyl radicals containing three or four carbon atoms and includes methyl, ethyl, propyl, isopropyl, butyl, isobutyl and tertiary butyl.

The term "proton acceptor" as used herein means the inorganic bases, preferably the alkali metal hydroxides, carbonates and bicarbonates, for instance, sodium hydroxide, potassium hydroxide, sodium carbonate, sodium bicarbonate or potassium carbonate; as well as the organic bases or amines, for instance; triethylamine, pyridine or N-ethyl-morpholine.

The compounds of formula I form salts with suitable therapeutically acceptable inorganic and organic bases. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the therapeutically acceptable alkali metals or alkaline earth metals, for example, sodium, potassium, magnesium, calcium and the like. Suitable organic bases include the following amines; benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxylakyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkylalkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administeration they may be used in the form of a sterile solution, preferably of pH 7.2–7.6 containing a pharmaceutically acceptable buffer.

The dosage of the present therapeutic agents will vary with the form administration and the particular compound chosen. Furthermore, it will vary with the particular host under treatment. Generally, treatment is initiated with small dosages substantially less than the optimal dose of the compound. Thereafter, the dosage is increased by small increments until the optimal effect under the circumstances is reached. In general, the compounds of this invention are most desirably administered at a concentration level that will generally afford effective results without causing any harmful or deleterious side effects. For topical administration a 0.05–0.2% solution may be administered dropwise to the eye. The frequency of installation varies with the subject under treatment from a drop every two or three days to once daily. For oral or parenteral administration a preferred level of dosage ranges from about 0.1 mg to about 200 mg per kilo of body weight per day, although aforementioned variations will occur. However, a dosage level that is in the range of from about 3.0 mg to about 30 mg per kilo of body weight per day is most satisfactory.

Unit dosage forms such as capsules, tablets, pills and the like may contain from about 5 mg to about 50 mg of the active ingredients of this invention, dependent on the type of unit dosage, preferably with a significant quantity of a pharmaceutical carrier. Thus, for oral administration, capsules can contain from between about 5 mg to about 50 mg of the active ingredients of this invention with or without a pharmaceutical diluent. Tablets, either effervescent or noneffervescent, can contain between about 5 to 50 mg of the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents, for example, maize starch and alginic acid and lubricating agents for example, magnesium stearate.

Syrups or elixirs suitable for oral administration can be prepared from water soluble salts, for example, sodium 1-oxo-3-thioxo-1H-benz[de]isoquinoline-2(3H)-acetate, and may advantageously contain glycerol and ethyl alcohol as solvents or preservatives.

The compound of formula I, or a therapeutically acceptable salt thereof, also can be used in combination with insulin or oral hypoglycemic agents to produce beneficial effect in the treatment of diabetes mellitus. In this instance, commercially available insulin preparations or oral hypolycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 32 ed., Medical Economics Co., Oradell, N.J., U.S.A., 1978. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the benzisoquinoline acetic acid derivatives of formula I and their pharmaceutically acceptable salts with an organic or inorganic base may be demonstrated by employing an in vitro testing procedure similar to that described by S. Hayman and J. H. Kinoshita, J. Biol. Chem., 240, 877 (1965). In the present case the procedure of Hayman and Kinoshita is modified in that the final chromatography step is omitted in the preparation of the enzyme from bovine lens.

The following results were obtained when the compounds of this invention were evaluated in the above in vitro test (the results for 1,3-dioxo-1H-benz-[de]isoquinoline-2(3H)-acetic acid, see U.S. Pat. No. 3,821,383 cited hereinbefore, also are included for comparative purposes):

| Compound | Concentration (Mole/l) | Percent Inhibition |
|---|---|---|
| 1,3-dioxo-1H-benz[de]- | $10^{-5}$ | 74 |
| isoquinoline-2(3H)- | $10^{-6}$ | 32 |
| acetic acid | $10^{-7}$ | 5 |
| (U.S. Pat. No. 3,821,383) | | |
| 1-oxo-3-thioxo-1H-benz- | $10^{-5}$ | 89 |
| [de]isoquinoline-2(3H)- | $10^{-6}$ | 75 |
| acetic acid | $10^{-7}$ | 28 |
| 1:1 mixture by weight of 1-oxo- | $10^{-5}$ | 88 |

-continued

| Compound | Concentration (Mole/l) | Percent Inhibition |
|---|---|---|
| 3-thioxo-6-(phenylthio)-1H-benz[de]isoquinoline-2(3H)-acetic acid and 3-oxo-1-thioxo-6-(phenylthio)-1H-benz[de]isoquinoline-2(3H)-acetic acid | $10^{-6}$ | 78 |
| | $10^{-7}$ | 35 |

The aldose reductase inhibiting property of the compound of this invention and its utilization in diminishing and alleviating diabetic complications also are demonstrable in experiments using galactosaemic rats, see Dvornik et al., cited above. Such experiments are exemplified hereinbelow after the listing of the following general comments pertaining to these experiments:

(a) Four or more groups of six male rats, 50–70 g, Sprague-Dawley strain, were used. The first group, the control group, was fed a mixture of laboratory chow (rodent laboratory chow, Purina) and glucose at 20% (W/W %) concentration. The untreated galactosaemic group was fed a similar diet in which galactose is substituted for glucose. The third group was fed a diet prepared by mixing 7 g of the known compound, 1,3-dioxo-1H-benz[de]isoquinoline-2(3H)-acetic acid, per kilogram of the galactose containing diet. The fourth (and fifth group if present) was fed a diet containing various amounts of 1-oxo-3-thioxo-1H-benz[de]isoquinoline-2(3H)-acetic acid in the galactose containing diet. The concentration of galactose in the diet of the treated groups was the same as that for the untreated galactosaemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues were frozen and kept up to two weeks before being analyzed for dulcitol.

(c) The polyol determination was performed by a modification of the procedure of M. Kraml and L. Cosyns, Clin. Biochem., 2, 373 (1969). Only two minor reagent changes were made: (a) The rinsing mixture was an aqueous 5% (w/v) trichloroacetic acid solution and (b) the stock solution was prepared by dissolving 25 mg of dulcitol in 100 ml of an aqueous trichloroacetic acid solution. [N.B.: For each experiment the average value found in the tissue from rats fed the glucose diet was substracted from the individual values found in the corresponding rat tissue to obtain the amount of polyol accumulated].

The following experiments show that the compound of this invention, 1-oxo-3-thioxo-1H-benz[de]isoquinoline-2(3H)-acetic acid, diminishes and alleviates the accumulation of dulcitol in the lenses and sciatic nerves of rats fed galactose as compared to an untreated animal and is more active than the known compound, 1,3-dioxo-1H-benz[de]isoquinoline-2(3H)-acetic acid. The results obtained in three separate experiments are exemplified in Table I.

TABLE 1

| | | Galactoanemic Rats | | Dulcitol Accumulation | | | | |
|---|---|---|---|---|---|---|---|---|
| | | | | Lenses | | | Sciatic Nerves | |
| Experiment | Treatment | Dose mg/kg/day | µg/mg | Percent Decrease | "t" test | µg/mg | Percent Decrease | "t" test |
| 1. | — | — | 10.35 ± 0.54 | | | 1.60 ± 0.32 | | |

TABLE 1-continued

| | Galactoanemic Rats | | Dulcitol Accumulation | | | | | |
| | | | Lenses | | | Sciatic Nerves | | |
| Experiment | Treatment | Dose mg/kg/day | μg/mg | Percent Decrease | "t" test | μg/mg | Percent Decrease | "t" test |
| --- | --- | --- | --- | --- | --- | --- | --- | --- |
| | 1,3-dioxo-1H-benz-[de]isoquinoline-2(3H)-acetic acid | 945 | 8.01 ± 0.86 | 23% | .05>P>.02 | 0.61 ± 0.19 | 62% | .05>P>.02 |
| | 1-oxo-3-thioxo-1H-benz-[de]isoquinoline-2(3H)-acetic acid | 371 | 5.84 ± 1.25 | 53% | .01>P>.001 | 0.09 ± 0.12 | 94% | .01>P>.001 |
| 2. | — | — | 10.30 ± 0.53 | | | 1.70 ± 0.13 | | |
| | 1,3-dioxo-1H-benz-[de]isoquinoline-2(3H) acetic acid | 980 | 7.67 ± 0.20 | 25% | P<.001 | 0.62 ± 0.05 | 64% | P<.001 |
| | 1-oxo-3-thioxo-1H-benz-[de]isoquinoline-2(3H)-acetic acid | 150 | 7.70 ± 0.34 | 28% | .01>P>.001 | 0.48 ± 0.06 | 72% | P<.001 |
| | 1-oxo-3-thioxo-1H-benz-[de]isoquinoline-2(3H)-acetic acid | 56 | 9.25 ± 0.57 | 10% | P>.05 | 1.03 ± 0.12 | 39% | .01>P>.001 |
| 3. | — | — | 8.89 ± 0.38 | | | 1.25 ± 0.08 | | |
| | 1,3-dioxo-1H-benz-[de]isoquinoline-2(3H)-acetic acid | 973 | 8.71 ± 0.59 | 2% | P>.05 | 0.53 ± 0.08 | 57% | P<.001 |
| | 1-oxo-3-thioxo-1H-benz[de]isoquinoline-2(3H)-acetic acid | 115 | 8.48 ± 0.34 | 5% | P>.05 | 0.47 ± 0.06 | 62% | P<.001 |

1-Oxo-3-thioxo-1H-benz[de]isoquinoline-2(3H)-acetic acid, or its therapeutically acceptable salt, also possess blood glucose lowering properties and an ability to stimulate insulin release in a diabetic subject, as described in greater detail in the aforementioned U.S. patent application Ser. No. 92,398 of W. Lippmann and K. Sestanj. The same compound also has properties beneficial for the treatment of hyperchlorhydria, as described in greater detail in the aforementioned patent application Ser. No. 92,605 of W. Lippmann.

PROCESS OF PREPARATION

The compounds of this invention are prepared by a process which is illustrated by the following reaction scheme in which X, Y and Z are as defined hereinbefore and R is lower alkyl:

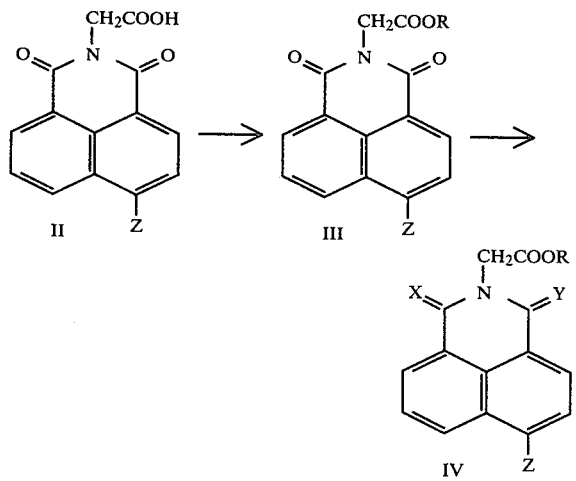

The starting material of formula II in which Z is hydrogen is known, for instance see U.S. Pat. No. 3,821,383 noted above. The starting material of formula II in which Z is phenylthio is prepared by reacting 4-chloro-1,8-naphthalic acid anhydride, a readily available starting material for instance see "Catalog Handbook of Fine Chemicals", 1979-1980, Aldirch Chemical Co., Inc., Milwaukee, Wisc., U.S.A., with glycine in the presence of a proton acceptor for example sodium hydroxide, potassium carbonate or triethylamine, to obtain 6-chloro-1,3-dioxo-1H-benz[de]isoquinoline-2(3H)-acetic acid, followed by reacting the latter compound with thiophenol in the presence of a proton acceptor.

With reference to the reaction scheme, the material of formula II is esterified to give the ester of formula III. Conventional esterification methods can be used. Preferred esterification conditions involve reacting the starting material with a lower alkanol, for example, methanol, ethanol or n-propanol, in the presence of a suitable acid catalyst, for example, p-toluenesulfonic acid, hydrochloric acid, sulfuric acid, perchloric acid or boron trifluoride etherate.

The choice of temperature and duration of the reaction time for performing the esterification is not critical but is largely dependent on the catalyst and lower alkanol used for the reaction. Usually it is more convenient to carry out the reaction at temperatures ranging from 20° C. to the boiling point of the mixture for a period of 15 minutes to 24 hours.

Thereafter, the ester of formula III is reacted under anhydrous conditions with about two to five moles of phosphorus pentasulfide in an inert solvent, e.g. xylene or toluene, to obtain the corresponding thioxoester of formula IV. This reaction is performed conveniently at temperatures ranging from 80° to about 150° C. and times ranging from 20 minutes to four hours. This reaction also can be performed in the presence of an organic base for instance, N-ethyl morpholine or pyridine.

Finally, the thioxoester of formula IV is hydrolyzed with a hydrolyzing agent to give the desired product of formula I. Generally speaking, this conversion is most conveniently performed by employing a base as the hydrolyzing agent. The hydrolysis is performed in the presence of sufficient water, followed by acidification of the reaction mixture to yield the desired acid. However, it should be understood that the manner of hydrolysis for the process of this invention is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1967, pp. 615–617), are also applicable.

For basic hydrolysis, a preferred embodiment involves subjecting the lower alkyl ester to the action of a strong base, for example, sodium or potassium hydroxide, in the presence of sufficient water to effect hydrolysis of the ester. The hydrolysis is performed using a suitable solvent, for example, methanol or ethanol.

The reaction mixture is maintained at a temperature of from 25° C. to the reflux temperature until hydrolysis occurs. Usually from 10 minutes to 6 hours is sufficient for this hydrolysis. The reaction mixture is then rendered acidic with an acid, for example, acetic acid, hydrochloric acid, sulfuric acid and the like, to release the free acid as a solid.

The following examples illustrate further this invention.

EXAMPLE 1

1,3-Dioxo-6-(phenylthio)-1H-benz[de]isoquinoline-2(3H)-acetic Acid

4-Chloro-1,8-naphthalic anhydride (20.0 g, 0.086 mole; commercial material purified by crystallization from toluene) was suspended in an aqueous 1 N sodium hydroxide solution (95 ml) of glycine (3.8 g, 0.095 mole). The mixture was stirred and refluxed for one hr, after which time a clear solution had resulted. The mixture was rendered acidic with conc hydrochloric acid. The resulting precipitate was collected and dried. Crystallization of the precipitate from anhydrous ethanol afforded 18.5 g of 6-chloro-1,3-dioxo-1H-benz[de]isoquinoline-2(3H)-acetic acid, mp 260° C.; UV (MeOH) 235,339 and 352 nm, $\epsilon$=41,310, 15,190 and 13,700, respectively; IR (CHCl$_3$) 1725, 1705 and 1670 cm$^{-1}$; NMR (DMSO-d$_6$) $\delta$4.6 (s, 2H), 6.0 (m, 1H), 7.9 (m, 2H), 8.45 (m, 3H); Anal. Calc'd.: C, 58.05%; H, 2.78%; N, 4.83%; Found: C, 58.16%; H, 2.74%; N, 4.69%.

The latter compound (15 g, 0.052 mole), anhydrous potassium carbonate (7.16 g, 0.052 moles), thiophenol (6.28 g, 5.9 ml, 0.057 mole) and distilled dimethylformamide (250 ml) were heated at reflux for one hr. An additional amount (0.6 g) of thiophenol was added and the mixture was heated at reflux for 0.5 hr. At this point an additional amount (0.7 g) of anhydrous potassium carbonate was added and the mixture heated at reflux for another 0.5 hr. The mixture now was poured into water (1 liter), cooled in an ice-bath and rendered acidic with conc hydrochloric acid (15 ml). The yellow precipitate was collected, washed with water and diethyl ether and then dried. Crystallization of the dried precipitate from glacial acetic acid gave 15.0 g of the title compound; mp 250–253° C.; UV (MeOH) 232, 250 and 345 nm, $\epsilon$=25,800, 19,625 and 7,340, respectively; IR(CHCl$_3$)~3000 (broad), 1740, 1690, 1648 cm$^{-1}$; NMR $\delta$4.66 (s, 2H), ~7.45 (s, 5H), 7.25 (d, 1H, J=8 Hz), 7.86 (d, 1H, J=8 Hz), ~8.4 (m, 3H); Anal. Calc'd.: C, 66.11%; H, 3.61%, N, 3.86%; Found: C, 66.26%; H, 3.70%, N, 3.69%.

EXAMPLE 2

1,3-Dioxo-6-(phenylthio)-1H-benz[de]isoquinoline-2(3H)-acetic Acid Ethyl Ester (III, Z=SPh and R=C$_2$H$_5$)

1,3-Dioxo-6-(phenylthio)-1H-benz[de]isoquinoline-2(3H)-acetic acid (3.55 g, 9.77 mmoles; described in Example 1), anhydrous pure ethanol (12 ml), toluene (30 ml) and p-toluenesulfonic acid hydrate (0.2 g) were heated at reflux for 16 hr in a Soxhlet apparatus in which the thimble was filled with hydrated alkali-aluminium silicate (3 A Molecular Sieves). The resulting clear mixture was washed with water (2×80 ml), 5% sodium bicarbonate (2×80 ml) and brine (100 ml), dried (MgSO$_4$) and concentrated to dryness. The residue was crystallized from isopropyl ether-carbon tetrachloride (1:1, 60 ml) to give 2.85 g of the title compound; mp 132°–134° C.; UV (MeOH) 231 and 344 nm, $\epsilon$=25,170 and 7,360 respectively; IR (CHCl$_3$) 1743, 1695 and 1660 cm$^{-1}$; NMR (CDCl$_3$) $\delta$1.25 (t, 3H, J=7 Hz), 4.15 (q, 2H, J=7 Hz), 4.85 (s, 2H), 7.15–8.65 (m, 10H); Anal. Calc'd.: C, 67.50%; H, 4.38%; N, 3.58%; Found: C, 67.87%; H, 4.44%; N, 3.50%.

EXAMPLE 3

1 (or 3)-Oxo-3 (or 1)-thioxo-6-(phenylthio)-1H-benz[de]isoquinoline-2(3H)-acetic Acid Ethyl Ester (IV, X=O (or S), Y=S (or O) and Z=SPh)

1,3-Dioxo-6-(phenylthio)-1H-benz[de]isoquinoline-2(3H)-acetic acid ethyl ester (3.7 g, 9.45 mmoles, described in Example 2, phosphorus pentasulfide (6.3 g, 28.4 mmoles), N-ethylmorpholine (10 ml) and dry toluene (20 ml) were heated at reflux for 4 hr and then stirred for 1 hr at 20° C. Two more additions of phosphorus pentasulfide (2.1 g each) were made and each time the mixture was heated at reflux for 2 hr thereafter. The solvent was removed. Water (200 ml) was added to the residue. The aqueous mixture was extracted with chloroform (600 ml). The extract was washed with dilute hydrochloric acid (2×100 ml) brine and dried (MgSO$_4$). Evaporation of the extract solvent gave a residue which was subjected to chromatography on silica gel (eluent=toluene: ethyl acetate: chloroform::7:0.5:2.5). Evaporation of the eluate gave 1.0 g of a 1:1 mixture of the two title compounds. This mixture of isomers had mp 115°–118° C.; UV (MeOH) 264 and 346 nm, $\epsilon$=21,140 and 5,780 cm$^{-1}$; IR (CHCl$_3$) 1745, 1685 cm$^{-1}$; M+407; Anal. Calc'd.: C, 64.84%; H, 4.20%; N, 3.44%; Found: C, 64.19%; H; 4.22%; N, 3.45%.

EXAMPLE 4

1 (or 3)-Oxo-3 (or 1)-thioxo-6-(phenylthio)-1H-benz[de]isoquinoline-2(3H)-acetic Acid (I; X=O (or S); Y=S (or O) and Z=SPh)

The mixture of isomers, mp 115°–118° C., 0.5 g, described in Example 3, was dissolved in dry, peroxide free, dioxane (30 ml) containing 5 ml of conc hydrochloric acid. The solution was heated at reflux under nitrogen for 48 hr. The solvent was evaporated and the residue triturated with water. The resultant solid was collected by filtration. The solid was dissolved in sodium bicarbonate solution (pH 7.2–7.3). The clear solution was acidified to pH 3. The precipitate was collected on a filter and dried. The final purification was achieved by column chromatography using silica gel (eluent-ethyl acetate: pyridine: acetic acid: water: :100:8:6:4). Evaporation of the eluate and crystallization of the residue from isopropyl alcohol gave 118 mg of a 1:1 mixture of the two title compounds. The mixture of isomers had mp 257°–263° C.; UV (MeOH) 251, 263 and 384 nm, $\epsilon=19{,}050$, 20,340 and 5,920, respectively; IR (CHCl$_3$) 3000, 1700 and 1680 cm$^{-1}$ M+379; NMR (CDCl$_3$) 5.25 (s, 2H), 7.0–9.1 (m, 10H); Anal. Calc'd.: C, 63.31%; H, 3.45%; N, 3.69%; Found: C, 61.56%; H, 3.58%; N, 3.40%.

The mixture of isomers can be separated by chromatography methods such as high pressure liquid chromatography or thin layer chromatography on silica gel using chloroform: methanol: acetic acid: : 85:10:5 as solvent.

EXAMPLE 5

1,3-Dioxo-1H-benz[de]isoquinoline-2(3H)-acetic Acid Ethyl Ester (III, Z=H and R=C$_2$H$_5$)

A mechanically-stirred mixture of 1,3-dioxo-1H-benz[de]isoquinoline-2(3H)-acetic acid (125.0 g, 0.49 mole), p-toluenesulfonic acid hydrate (9.3 g, 0.049 mole), anhydrous pure ethanol (226 g, 288 ml, 0.49 mole) and dry toluene (750 ml) was heated at reflux for 16 hr in a Soxhlet apparatus in which the thimble was filled with hydrated alkali-aluminium silicate (3 A Molecular Sieves). The title compound was crystallized from the reaction mixture after cooling to room temperature. The crystals were collected and a second crop of crystals were obtained from the mother liquors. Recrystallization of the two crops of crystals from ethyl acetate gave the title compound; mp 160°–162° C.; UV (MeOH) 232, 332 and 341 nm, $\epsilon=48{,}613$, 13,470 and 12,920, respectively; IR (CHCl$_3$) 1745, 1705 and 1665 cm$^{-1}$; Anal. Calc'd.: C, 67.84%; H, 4.63%; N, 4.94%; Found: C, 67.89%; H, 4.60%; N, 4.87%.

EXAMPLE 6

1-Oxo-3-thioxo-1H-benz[de]isoquinoline-2(3H)-acetic Acid Ethyl Ester (IV; X=O, Y=S and Z=H)

Under anhydrous conditions, a stirred suspension of 1,3-dioxo-1H-benz[de]-isoquinoline-2(3H)-acetic acid ethyl ester (120 g. 0.42 mole, described in Example 5, and phosphorus pentasulfide (283 g, 1.27 mole) in dry xylene (1800 ml) was heated at reflux for one hr. The solvent was evaporated. The residue was suspended in water (1800 ml) and N-ethylmorpholine (15 ml) for 18 hr. The insoluble material was collected, dissolved in 800 ml of chloroform and the solution dried (MgSO$_4$). The solution was evaporated to dryness and the residue subject to purification on a column of silica gel (eluent=chloroform). Elution of the chromatographic column and evaporation of the eluate first gave the corresponding dithioxo by-product, i.e. formula IV in which both X and Y=S and Z=H), mp 103°–105° C. (recrystallized from carbon tetrachloride), and then the title compound, mp 150°–151° C.; UV (MeOH) 244, 250, 330 and 345 nm, $\epsilon=23{,}280$; 21,260; 8,895 and 8,170, respectively; IR (CHCl$_3$) 1745, 1686, 1585 cm$^{-1}$; M+299; NMR (CDCl$_3$) $\delta$1.35 (t, 3H, J=7 Hz), 4.25 (q, 2H, J=7 Hz), 5.55 (s, 2H), 7.55–9.0 (m, 6H); Anal. Calc'd: C, 64.20%; H, 4.38%; N, 4.68%; Found: C, 64.66%; H, 4.40%; N, 4.57%.

EXAMPLE 7

1-Oxo-3-thioxo-1H-benz[de]isoquinoline-2(3H)-acetic Acid (I:X=O, Y=S and Z=H)

A suspension of 1-oxo-3-thioxo-1H-benz[de]isoquinoline-2(3H)-acetic acid ethyl ester (34.35 g, 0.115 mole, described in Example 6) in methanol (200 ml) and aqueous 4 N sodium hydroxide (43 ml, 0.1721 mole) was stirred at 20° C. for 18 hr. The solvent was removed and the residue suspended in water (1 liter). The aqueous suspension was extracted with ethyl acetate (2×1 liter) to remove unreacted ethyl ester. The aqueous phase was rendered acidic with 2 N hydrochloric acid. The resulting precipitate was collected. Recrystallization of the precipitate from methanol gave 22.5 g of the title compound, mp 265° C. (dec.); UV (MeOH) 244, 251, 333, 344, 390 nm, $\epsilon=20{,}210$, 19,150, 8,640, 8,225, 13,995, respectively; IR (nujol) 2900, 1720 and 1683 cm$^{-1}$; NMR (DMSO-d$_6$) $\delta$5.33 (s, 2H), 7.3–8.93 (m, 6H); Anal. Calc'd.: C, 61.98%; H, 3.34%; N, 5.16%; Found: C, 62.07%; H, 3.42%, N, 5.00%.

We claim:

1. A compound of the formula

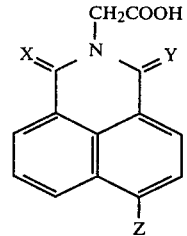

in which X and Y are independently O or S, with the proviso both are not O or S, and Z is H or thiophenyl, or a therapeutically acceptable salt thereof, with an organic or inorganic base.

2. 1-Oxo-3-thioxo-1H-benz[de]isoquinoline-2-(3H)-acetic acid, as claimed in claim 1.

3. 1-Oxo-3-thioxo-6-(phenylthio)-1H-benz[de]isoquinoline-2(3H)-acetic acid, as claimed in claim 1.

4. 3-Oxo-1-thioxo-6-(phenylthio)-1H-benz[de]isoquinoline-2(3H)-acetic acid, as claimed in claim 1.

5. A pharmaceutical composition for preventing or relieving diabetic complications consisting of cataracts, neuropathy, nephropathy and retinopathy in a diabetic mammal which comprises an effective amount of a compound of claim 1, or a pharmaceutically acceptable salt thereof with an organic or inorganic base, and a pharmaceutically acceptable carrier.

6. The pharmaceutical composition of claim 5 which also comprises an oral hypoglycemic agent selected from the group consisting of acetohexamide, chlorpropamide, tolazamide, tolbutamide and phenformin.

7. A method of preventing or relieving diabetic complications consisting of cataracts, neuropathy, nephropathy and retinopathy in a diabetic mammal which comprises administering to said mammal an alleviating or prophylactic amount of a compound of claim 1, or a therapeutically acceptable salt thereof with an organic or inorganic base.

8. The method of claim 7 in which the administration is performed simultaneously or sequentially with the administration of an effective blood glucose lowering amount of insulin or said an oral hypoglycemic agent, selected from the group consisting of acetohexamide, chlorpropamide, tolazamide, tolbutamide and phenformin.

* * * * *